United States Patent
Hwang et al.

(10) Patent No.: US 11,583,825 B2
(45) Date of Patent: Feb. 21, 2023

(54) APPARATUS FOR PREPARING OLIGOMER

(71) Applicant: LG CHEM, LTD., Seoul (KR)

(72) Inventors: Moon Sub Hwang, Daejeon (KR); Jeong Seok Lee, Daejeon (KR); Jong Hun Song, Daejeon (KR); You Na Kim, Daejeon (KR); Hong Min Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 17/297,291

(22) PCT Filed: Aug. 7, 2020

(86) PCT No.: PCT/KR2020/010464
§ 371 (c)(1),
(2) Date: May 26, 2021

(87) PCT Pub. No.: WO2021/118008
PCT Pub. Date: Jun. 17, 2021

(65) Prior Publication Data
US 2022/0055010 A1 Feb. 24, 2022

(30) Foreign Application Priority Data
Dec. 9, 2019 (KR) .................. 10-2019-0162692

(51) Int. Cl.
*B01J 19/26* (2006.01)
*B01J 4/00* (2006.01)
*B01D 3/06* (2006.01)

(52) U.S. Cl.
CPC .............. *B01J 19/26* (2013.01); *B01D 3/06* (2013.01); *B01J 4/001* (2013.01); *B01J 2204/005* (2013.01)

(58) Field of Classification Search
CPC ........ B01J 19/24; B01J 19/0013; B01J 19/26; B01J 4/001; B01J 2204/005
See application file for complete search history.

(56) References Cited

U.S. PATENT DOCUMENTS

| 4,058,652 A | 11/1977 | Smith et al. |
| 4,222,986 A * | 9/1980 | Smith ...................... B01J 19/18 422/135 |
| 5,922,190 A | 7/1999 | Guitian et al. |
| 2005/0020866 A1* | 1/2005 | Kobayashi .............. C08F 10/00 585/502 |

(Continued)

FOREIGN PATENT DOCUMENTS

| CN | 2725728 Y | 9/2005 |
| CN | 2771179 Y | 4/2006 |

(Continued)

*Primary Examiner* — Lessanework Seifu
(74) *Attorney, Agent, or Firm* — Dentons US LLP

(57) ABSTRACT

The present disclosure provides an apparatus for preparing oligomer including: a reactor; a gas-liquid separator; a solvent transfer line; a second transfer line; a first spray nozzle unit; and a second spray nozzle unit. The apparatus is capable of improving stability of the entire process by including a first spray nozzle unit and a second spray nozzle unit in a reactor and thus preventing by-products containing polymer substances such as C20+ from being entrained with a desired product during a reaction.

6 Claims, 1 Drawing Sheet

(56) References Cited

U.S. PATENT DOCUMENTS

2018/0030181 A1     2/2018  Emoto

FOREIGN PATENT DOCUMENTS

| EP | 0024933 | A2 | 3/1981 |
| EP | 0024933 | A3 | 3/1981 |
| KR | 10-2004-0062550 | A | 7/2004 |
| KR | 10-2015-0051190 | A | 5/2015 |
| KR | 10-2017-0028203 | A | 3/2017 |
| KR | 10-2017-0058935 | A | 5/2017 |
| WO | 2018116176 | A1 | 6/2018 |
| WO | 2018/122704 | A1 | 7/2018 |

* cited by examiner

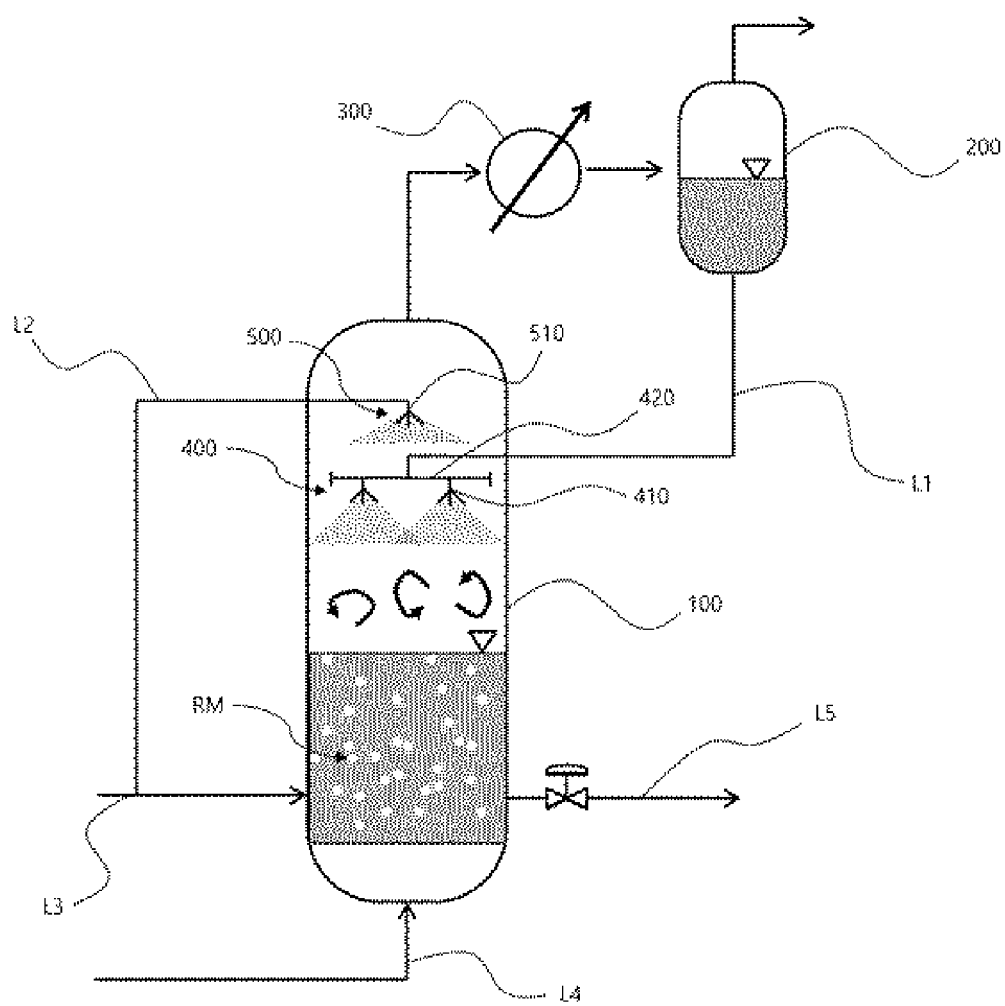

APPARATUS FOR PREPARING OLIGOMER

CROSS-REFERENCE TO RELATED APPLICATIONS

The present application is a National Phase entry pursuant to 35 U.S.C. § 371 of International Application No. PCT/KR2020/010464, filed on Aug. 7, 2020, and claims the benefit of and priority to Korean Patent Application No. 10-2019-0162692, filed on Dec. 9, 2019, the disclosures of which are incorporated by reference in their entirety for all purposes as if fully set forth herein.

TECHNICAL FIELD

The present invention relates to an apparatus for preparing oligomer, and more particularly, to an apparatus for preparing oligomer capable of improving stability of the entire process by reducing the amount of entrainment of solids and liquids inside a reactor when producing an oligomer.

BACKGROUND ART

An alpha olefin is an important substance used for a comonomer, a cleaner, a lubricant, a plasticizer, or the like, and has been used commercially widely used. In particular, 1-hexene and 1-octene have been frequently used as a comonomer to control a density of polyethylene when producing linear low-density polyethylene (LLDPE).

The alpha olefin such as 1-hexene or 1-octene typically has been produced through an oligomerization reaction of ethylene. The oligomerization reaction of ethylene is performed through an oligomerization reaction (a trimerization reaction or a tetramerization reaction) of ethylene in the presence of a catalyst using ethylene as a reactant. As a product produced through the reaction, a small amount of by-products containing polymer substances such as C20+ are produced during a catalytic reaction, in addition to a multi-component hydrocarbon mixture containing a desired 1-hexene and 1-octene. The by-products accumulate not only on an inner wall of a reactor but also in devices for subsequent processes of the reactor such as a condenser, a pipe, and a valve, which causes fouling. As such, in a case where the fouling occurs in the devices for the subsequent processes of the reactor, performance degradation and mechanical damage of the devices are caused, and in the worst case, operations of the entire processes are required to be shut down. Thus, a production amount is reduced due to a reduction of operating time, and a cost required in a cleaning process increases.

Therefore, in order to solve the above problems, it is required to conduct studies to reduce the amount of entrainment of solids containing polymers and liquids in a reactor.

DISCLOSURE

Technical Problem

In order to solve the problems mentioned in the background art, an object of the present invention is to provide an apparatus for preparing oligomer capable of improving stability of the entire process by including a first spray nozzle unit and a second spray nozzle unit in a reactor and thus preventing by-products containing polymer substances such as C20+ from being entrained with a desired product during a reaction.

Technical Solution

In one general aspect, an oligomer production apparatus includes: a reactor receiving a monomer stream and a solvent stream, allowing an oligomerization reaction to proceed, and discharging a gaseous first discharge stream and a liquid second discharge stream; a gas-liquid separator separating the first discharge stream of the reactor into a liquid phase and a gas phase and feeding a liquid bottom discharge stream to the reactor; a first transfer line extending from a bottom of the gas-liquid separator to a region spaced apart from an inner wall of the reactor at a position higher than a reaction region inside the reactor and transferring the bottom discharge stream of the gas-liquid separator; a solvent transfer line transferring the solvent stream to the reactor; a second transfer line separated from the solvent transfer line and transferring a part of the solvent stream to a region spaced apart from the inner wall of the reactor at a position higher than a height at which the first transfer line inside the reactor is formed; a first spray nozzle unit connected to an end of the first transfer line inside the reactor and having n spray nozzles formed to be spaced apart from each other (n is an integer of 2 or more); and a second spray nozzle unit connected to an end of the second transfer line inside the reactor and having n−1 spray nozzles formed to be spaced apart from each other (n is an integer of 2 or more).

Advantageous Effects

According to the apparatus for preparing oligomer of the present invention, the first spray nozzle unit is formed at the position higher than the reaction region inside the reactor and the bottom discharge stream of the gas-liquid separator is sprayed through the first spray nozzle unit, such that entrainment of solid non-vapor containing a polymer substance having a relatively heavy weight can be removed.

Further, according to the present invention, the second spray nozzle unit is formed at the position higher than the height at which the first spray nozzle unit is formed and the solvent is sprayed through the second spray nozzle unit, such that residual liquid non-vapor which is not removed through the first spray nozzle unit and has a relatively light weight can be additionally removed.

Further, according to the present invention, the amount of entrainment of solid and liquid non-vapor in the reactor is reduced, such that the stability of the entire process can be improved.

DESCRIPTION OF DRAWINGS

FIG. 1 is a process flow diagram of an apparatus for preparing oligomer according to an exemplary embodiment of the present invention.

BEST MODE

The terms and words used in the description and claims of the present invention are not to be construed as general or dictionary meanings but are to be construed as meanings and concepts meeting the technical ideas of the present invention based on a principle that the inventors can appropriately define the concepts of terms in order to describe their own inventions in the best mode.

The term "stream" in the present invention may refer to a flow of a fluid in a process, and may also refer to a fluid flowing through a transfer line (pipe) itself. Specifically, the "stream" may refer to both the fluid flowing through the pipe connecting respective devices to each other itself and the flow of the fluid at the same time. In addition, the fluid may refer to a fluid including at least one of gas, liquid, and solid.

The term "C#" in which "#" is a positive integer in the present invention refers to all hydrocarbons having # carbon atoms. Accordingly, the term "C10" refers to a hydrocarbon compound having 10 carbon atoms. In addition, the term "C#+" refers to all hydrocarbon molecules having # or more carbon atoms. Accordingly, the term "C10+" refers to a mixture of hydrocarbons having 10 or more carbon atoms.

Hereinafter, the present invention will be described in more detail with reference to FIG. 1 for assisting in understanding the present invention.

According to the present invention, there is provided an apparatus for preparing oligomer. As the apparatus for preparing oligomer, it is possible to provide an apparatus for preparing oligomer including: a reactor 100 receiving a monomer stream and a solvent stream, allowing an oligomerization reaction to proceed, and discharging a gaseous first discharge stream and a liquid second discharge stream; a gas-liquid separator 200 separating the first discharge stream of the reactor 100 into a liquid phase and a gas phase and feeding a liquid bottom discharge stream to the reactor 100; a first transfer line L1 extending from a bottom of the gas-liquid separator 200 to a region spaced apart from an inner wall of the reactor 100 at a position higher than a reaction region inside the reactor 100 and transferring the bottom discharge stream of the gas-liquid separator 200; a solvent transfer line L3 transferring the solvent stream to the reactor 100; a second transfer line L2 separated from the solvent transfer line L3 and transferring a part of the solvent stream to a region spaced apart from the inner wall of the reactor 100 at a position higher than a height at which the first transfer line L1 inside the reactor 100 is formed; a first spray nozzle unit 400 connected to an end of the first transfer line L1 inside the reactor 100 and having n spray nozzles 410 formed to be spaced apart from each other (n is an integer of 2 or more); and a second spray nozzle unit 500 connected to an end of the second transfer line L2 inside the reactor 100 and having n−1 spray nozzles 510 formed to be spaced apart from each other (n is an integer of 2 or more).

According to an exemplary embodiment of the present invention, the reactor 100 can be provided to allow an oligomerization reaction of a monomer to proceed in the presence of a catalyst and a solvent and thus to produce an oligomer product.

According to an exemplary embodiment of the present invention, the reactor 100 can be a reactor 100 suitable for a continuous process. Examples of the reactor 100 can include one or more reactors selected from the group consisting of a continuous stirred-tank reactor, a plug flow reactor, and a bubble column reactor. By this configuration, the oligomer product can be continuously produced.

According to an exemplary embodiment of the present invention, the monomer can include ethylene. Specifically, the monomer stream containing an ethylene monomer is fed to the reactor 100 and subjected to the oligomerization reaction, and thus, a desired alpha olefin product can be produced. In this case, the oligomerization reaction can be performed in a lower or middle region of the reactor 100. The oligomerization reaction of the monomer can be performed in a liquid reaction medium (RM) dissolved in a solvent in the presence of a catalyst or a cocatalyst. As such, the region composed of the reaction medium in which the oligomerization reaction of the monomer is performed can be defined as a reaction region. The oligomerization reaction can refer to a polymerization reaction of a small amount of monomers. The polymerization reaction is called trimerization or tetramerization depending on the number of monomers to be polymerized, and these polymerization reactions are collectively referred to as multimerization.

The alpha olefin is an important substance used for a comonomer, a cleaner, a lubricant, a plasticizer, or the like, and has been used commercially widely used. In particular, 1-hexene and 1-octene have been frequently used as a comonomer to control a density of polyethylene when producing linear low-density polyethylene (LLDPE). The alpha olefin such as 1-hexene or 1-octene can be produced, for example, through a trimerization reaction or tetramerization reaction of ethylene.

According to an exemplary embodiment of the present invention, the oligomerization reaction of the monomer can be performed by a homogeneous liquid phase reaction in the presence or absence of a solvent, a slurry reaction in which a catalyst is partially dissolved or not entirely dissolved, a two phase liquid/liquid reaction, a bulk reaction in which a product acts as a main medium, or a gas phase reaction, by applying the above reaction system and a general contact technology.

The solvent can be fed into the reactor 100 through the solvent transfer line L3. In this case, the solvent transfer line L3 can be formed on a lower side surface of the reactor 100 and can be formed at a position lower than the reaction region in the reactor 100.

The solvent can include one or more selected from the group consisting of n-pentane, n-hexane, n-heptane, cyclohexane, methylcyclohexane, octane, cyclooctane, decane, dodecane, benzene, xylene, 1,3,5-trimethylbenzene, toluene, ethylbenzene, chlorobenzene, dichlorobenzene, and trichlorobenzene.

The catalyst can include a transition metal source. Examples of the transition metal source can be a compound containing one or more selected from the group consisting of chromium(III) acetylacetonate, chromium(III) chloride tetrahydrofuran, chromium(III) 2-ethylhexanoate, chromium (III) tris(2,2,6,6-tetramethyl-3,5-heptanedionate), chromium (III) benzoylacetonate, chromium(III) hexafluoro-2,4-pentanedionate, chromium(III) acetate hydroxide, chromium(III) acetate, chromium(III) butyrate, chromium (III) pentanoate, chromium(III) laurate, and chromium(III) stearate.

Examples of the cocatalyst can include one or more selected from the group consisting of trimethylaluminium, triethylaluminium, triisopropylaluminium, triisobutylaluminum, ethylaluminum sesquichloride, diethylaluminum chloride, ethylaluminium dichloride, methylaluminoxane, modified methylaluminoxane, and borate.

According to an exemplary embodiment of the present invention, the monomer stream can be fed into the reactor 100 through the bottom of the reactor 100. For example, the monomer stream can be fed into the reactor 100 through a monomer transfer line L4 connected to the bottom of the reactor 100. In this case, the monomer stream can be fed to the reactor 100 in a gas state.

A gaseous monomer stream fed to the reactor 100 is subjected to the oligomerization reaction through a catalytic reaction while passing through the liquid reaction medium (RM) in which the solvent and the catalyst are present, and in this case, gas and liquid are mixed with each other as the reaction medium (RM) and present as two phases. The oligomer product produced through the oligomerization reaction of the monomer can be discharged through a product transfer line L5 as the liquid second discharge stream, and unreacted monomers which are subjected to no oligomerization reaction in the reaction medium (RM) can be discharged as the gaseous first discharge stream.

Specifically, the first discharge stream of the reactor 100 can contain the unreacted monomers and the solvent that are not involved in the oligomerization reaction of the monomer. As such, the first discharge stream containing the unreacted monomers and the solvent is fed to the gas-liquid separator 200 and is separated into a gas phase and a liquid phase, and the separated liquid substance is discharged as the bottom discharge stream of the gas-liquid separator 200. In this case, the bottom discharge stream of the gas-liquid separator 200 can be fed to the first spray nozzle unit 400 through a first transfer line to be described below.

In addition, the separated gaseous substance can be discharged as a top discharge stream of the gas-liquid separator 200. The top discharge stream of the gas-liquid separator 200 is a stream containing the unreacted monomers. The unreacted monomers can be separated from the top discharge stream of the gas-liquid separator 200 at a high purity level by a method such as distillation and then can be re-fed to the reactor 100. In this case, the unreacted monomers can be reused, and process efficiency can thus be improved.

In addition, the second discharge stream of the reactor 100 can contain the oligomer product produced through the oligomerization reaction of the monomer and the solvent. In this case, the oligomer product and the solvent can be separated from each other by an additional separator (not illustrated), and the separated solvent can be reused in an oligomer production process. In addition, as an example, in a case where the oligomerization reaction is performed by using an ethylene monomer as the monomer, the oligomer product can include 1-hexene and 1-octene.

In the reactor 100, solid polymers are produced as by-products in addition to the desired oligomer product through the catalytic reaction of the monomer, and the solid polymers are suspended in the liquid reaction medium (RM). In this case, the solid polymers and the liquid solvent are entrained with gaseous unreacted monomers by a rate at which a large amount of the gaseous monomer stream is introduced, and then discharged as the first discharge stream of the reactor 100. In this case, fouling occurs in devices for subsequent processes of the reactor 100 such as a condenser, a pipe, and a valve, due to adhesion of the polymer.

On the other hand, in the present invention, the first spray nozzle unit 400 and the second spray nozzle unit 500 are provided in the reactor 100, such that the by-products containing the polymer can be prevented from being entrained with the desired oligomer product during the reaction, and the fouling can thus be prevented from occurring in the devices for the subsequent processes, thereby improving the stability of the entire process.

According to an exemplary embodiment of the present invention, the first discharge stream of the reactor 100 can be discharged through a top of the reactor 100 and fed to the gas-liquid separator 200.

The gas-liquid separator 200 can receive the first discharge stream discharged through the top of the reactor 100 and can separate the first discharge stream into a liquid phase and a gas phase. As an example, a thin film evaporator, a falling film evaporator, or a flash drum can be used as the gas-liquid separator 200. As a specific example, the gas-liquid separator 200 can be a flash drum.

According to an exemplary embodiment of the present invention, the apparatus for preparing oligomer can further include a condenser 300 provided above the reactor 100. Specifically, the first discharge stream of the reactor 100 fed to the gas-liquid separator 200 can be fed to the gas-liquid separator 200 after passing through the condenser 300.

The first discharge stream of the reactor 100 can be partially liquefied while passing through the condenser 300. Specifically, a liquid phase and a gas phase are mixed with each other in the first discharge stream of the reactor 100 as the first discharge stream of the reactor 100 passes through the condenser 300, and thus, the first discharge stream of the reactor 100 is present as two phases. As such, the first discharge stream of the reactor 100 in which the liquid phase and the gas phase are mixed with each other is fed to the gas-liquid separator 200. In the gas-liquid separator 200, the liquid substance can be discharged as the bottom discharge stream and the gaseous substance can be discharged as the top discharge stream.

The gaseous substance discharged as the top discharge stream of the gas-liquid separator 200 can contain the unreacted monomer. In addition, the liquid substance discharged as the bottom discharge stream of the gas-liquid separator 200 can contain the solvent. In this case, the bottom discharge stream of the gas-liquid separator 200 can be re-fed into the reactor 100 through the first transfer line L1.

According to an exemplary embodiment of the present invention, the first transfer line L1 can extend from the bottom of the gas-liquid separator 200 to the region spaced apart from the inner wall of the reactor 100 at the position higher than the reaction region inside the reactor 100. For example, the end of the first transfer line L1 can extend to the central portion of the reactor 100. In this case, the first transfer line L1 can re-feed the bottom discharge stream of the gas-liquid separator 200 into the reactor 100.

According to an exemplary embodiment of the present invention, the apparatus for preparing oligomer can include the first spray nozzle unit 400 spraying the bottom discharge stream of the gas-liquid separator 200 transferred through the first transfer line L1 in the reactor 100.

The first spray nozzle unit 400 can be connected to the end of the first transfer line L1 and can have the n spray nozzles 410 formed to be spaced apart from each other (n is an integer of 2 or more). Specifically, the bottom discharge stream of the gas-liquid separator 200 can be fed to the first spray nozzle unit 400 through the first transfer line L1, and can be sprayed into the reactor 100 through the n spray nozzles 410 formed in the first spray nozzle unit 400.

As such, the bottom discharge stream of the gas-liquid separator 200 is sprayed through the first spray nozzle unit 400, such that entrainment of polymer non-vapor which is a solid substance having a relatively heavy weight in mixed vapor (vapor+non-vapor) rising in a non-uniform state by vortex can be preferentially removed.

The n spray nozzles 410 can be formed in the first spray nozzle unit 400, and n can be an integer of 2 to 20. This can mean that 2 to 20 spray nozzles 410 are formed in the first spray nozzle unit 400. For example, n can be 2 to 15, 2 to 10, or 2 to 5. n can be appropriately adjusted depending on a diameter of the reactor 100.

The n spray nozzles 410 formed in the first spray nozzle unit 400 can be formed to be spaced apart from each other at predetermined intervals. In this case, the intervals between the n spray nozzles 410 are not particularly limited, and can be appropriately adjusted so that a region in which the bottom discharge stream of the gas-liquid separator 200 sprayed from each of the n spray nozzles 410 are mixed with each other exists.

In this case, the n spray nozzles 410 can be formed on the same horizontal line. Specifically, the n spray nozzles 410 can be formed at the same height inside the reactor 100.

The bottom discharge stream of the gas-liquid separator 200 sprayed from the spray nozzles 410 that are adjacent to the inner wall of the reactor 100 among the n spray nozzles 410 can reach the inner wall of the reactor 100. For example, in a case where the number of the spray nozzles 410 formed in the first spray nozzle unit 400 is 2, as illustrated in FIG. 1, the two spray nozzles 410 are formed to be adjacent to the inner wall of the reactor 100 rather than the center of the reactor 100, such that the bottom discharge stream of the gas-liquid separator 200 sprayed from the spray nozzles 410 can be formed to reach the inner wall of the reactor 100.

The n spray nozzles 410 can be installed to spray the bottom discharge stream of the gas-liquid separator 200 toward the bottom of the reactor 100. By doing so, the non-vapor in the mixed vapor rising through the reaction medium (RM) inside the reactor 100 can be removed.

As such, the first spray nozzle unit 400 is formed, such that entrainment of the polymer non-vapor which is a solid substance having a relatively heavy weight in the mixed vapor (vapor+non-vapor) rising in a non-uniform state by vortex in the reactor 100 can be preferentially removed.

The first spray nozzle unit 400 can include a first nozzle pipe 420 connecting the n spray nozzles 410 formed in the first spray nozzle unit 400 and the first transfer line L1 to each other.

Specifically, the first nozzle pipe 420 distributes and feeds the bottom discharge stream of the gas-liquid separator 200 transferred through the first transfer line L1 to each of the n spray nozzles 410 formed in the first spray nozzle unit 400, and connects the n spray nozzles 410 to each other.

Each of the n spray nozzles 410 can include at least one spray port. In addition, the spray nozzle 410 can be implemented in a spray form including a plurality of spray ports. For example, the number of the spray port of the spray nozzle 410 can be 1 to 5, 1 to 4, or 2 to 4. Referring to FIG. 1, the spray nozzle 410 can be implemented in a form including three spray ports.

In the first spray nozzle unit 400, the n spray nozzles 410 can be arranged in a line at predetermined intervals at the first nozzle pipe 420.

As an example, the first nozzle pipe 420 can be formed in a straight or curved shape. In this case, the n spray nozzles 410 can be arranged in a line at predetermined intervals at the first nozzle pipe 420 having the straight or curved shape.

As another example, the first nozzle pipe 420 can be implemented into a polygonal shape such as a triangle, a circular shape, a radial shape, or the like. In this case, the arrangement of the n spray nozzles 410 can be changed in various forms depending on the shape of the first nozzle pipe 420 having the polygonal shape, the circular shape, the radial shape, or the like.

In the first spray nozzle unit 400, a pressure of the bottom discharge stream of the gas-liquid separator 200 sprayed through the n spray nozzles 410 can be 0.01 MPa to 1 MPa, 0.1 MPa to 0.5 MPa, or 0.1 MPa to 0.3 MPa. When the bottom discharge stream of the gas-liquid separator 200 is sprayed at the pressure within the above ranges, the entrainment of the non-vapor in the reactor 100 can be effectively removed.

According to an exemplary embodiment of the present invention, the apparatus for preparing oligomer can further include the second transfer line L2 transferring the part of the solvent stream into the reactor 100. Specifically, the second transfer line L2 can be separated from the solvent transfer line L3 transferring the solvent stream to the reactor 100 and can extend to the region spaced apart from the inner wall of the reactor 100 at the position higher than the height at which the first transfer line L1 inside the reactor 100 is formed. For example, the end of the second transfer line L2 can extend to the central portion of the reactor 100 located at a position higher than a height at which the end of the first transfer line L1 is formed. In this case, the second transfer line L2 can feed the solvent stream into the reactor 100.

A flow rate of the solvent stream separated through the second transfer line L2 to a total flow rate of the solvent stream fed through the solvent transfer line L3 can be 0.01 to 0.2. For example, the flow rate of the solvent stream separated through the second transfer line L2 to the total flow rate of the solvent stream fed through the solvent transfer line L3 can be 0.01 to 0.18, 0.05 to 0.18, or 0.05 to 0.15. Specifically, 1 wt % to 20 wt % of the total flow rate of the solvent stream fed through the solvent transfer line L3 can be fed into the reactor 100 through the second transfer line L2, and 80 wt % to 99 wt % of the total flow rate of the solvent stream fed through the solvent transfer line L3 can be fed into the reactor 100 through the solvent transfer line L3. As such, a part of the pure solvent can be fed into the reactor 100, and the entrainment in the reactor 100 can be removed.

According to an exemplary embodiment of the present invention, the apparatus for preparing oligomer can include the second spray nozzle unit 500 spraying the solvent stream transferred through the second transfer line L2 in the reactor 100.

The second spray nozzle unit 500 can be connected to the end of the second transfer line L2 and can have the n−1 spray nozzles 510 formed to be spaced apart from each other (n is an integer of 2 or more). Specifically, the solvent stream can be fed to the second spray nozzle unit 500 through the second transfer line L2, and can be sprayed into the reactor 100 through the n−1 spray nozzles 510 formed in the second spray nozzle unit 500.

As such, the solvent stream is sprayed through the second spray nozzle unit 500, such that residual non-vapor in a liquid state such as liquid droplets having a relatively light weight in the mixed vapor which rises to the central region of the reactor 100 and is not removed through the first spray nozzle unit 400 can be additionally removed.

The n−1 spray nozzles 510 can be formed in the second spray nozzle unit 500, and n can be an integer of 2 to 50. This can mean that 1 to 49 spray nozzles 510 are formed in the second spray nozzle unit 500. For example, n can be 2 to 30, 2 to 20, or 2 to 10. n can be appropriately adjusted depending on the diameter of the reactor 100.

When the number of the n−1 spray nozzles 510 formed in the second spray nozzle unit 500 is 2 or more, the spray nozzles 510 can be formed to be spaced apart from each other at predetermined intervals. In this case, the intervals between the n−1 spray nozzles 510 are not particularly limited, and can be appropriately adjusted so that the solvent stream sprayed from each of the n−1 spray nozzles 510 is sprayed to a region including a region between the $n^{th}$ and n−$1^{th}$ spray nozzles 410 of the first spray nozzle unit 400. Specifically, each of the n−1 spray nozzles 510 formed in the second spray nozzle unit 500 can be formed in a region between lines vertical to positions at which the $n^{th}$ and n−1th spray nozzles 410 of the first spray nozzle unit 400 are formed.

In this case, the n−1 spray nozzles 510 can be formed on the same horizontal line. Specifically, when the number of the n−1 spray nozzles 510 is 2 or more, the n−1 spray nozzles 510 can be formed at the same height inside the reactor 100.

The n−1 spray nozzles 510 can be installed to spray the solvent stream toward the bottom of the reactor 100. By doing so, the non-vapor in the mixed vapor rising through the reaction medium (RM) inside the reactor 100 can be removed.

As such, the second spray nozzle unit 500 is formed, such that the residual non-vapor in a liquid state such as liquid droplets having a relatively light weight in the mixed vapor which rises to the central region of the reactor 100 and is not removed through the first spray nozzle unit 400 can be additionally removed.

The second spray nozzle unit 500 can include a second nozzle pipe (not illustrated) connecting the n−1 spray nozzles 510 formed in the second spray nozzle unit 500 and the second transfer line L2 to each other.

Specifically, the second nozzle pipe (not illustrated) can feed the solvent stream transferred through the second transfer line L2 to each of the n−1 spray nozzles 510 formed in the second spray nozzle unit 500. For example, when the number of the n−1 spray nozzles 510 is 2 or more, the second nozzle pipe (not illustrated) distributes and feeds the solvent stream to each of the n−1 spray nozzles 510 and can connect the n−1 spray nozzles 510 to each other.

Each of the n−1 spray nozzles 510 can include at least one spray port. In addition, the spray nozzles 510 can be implemented in a spray form including a plurality of spray ports. For example, the number of the spray port of the spray nozzle 510 can be 1 to 5, 1 to 4, or 2 to 4. Referring to FIG. 1, the spray nozzle 510 can be implemented in a form including three spray ports.

In the second spray nozzle unit 500, the n−1 spray nozzles 510 can be arranged in a line at predetermined intervals at the second nozzle pipe (not illustrated).

As an example, the second nozzle pipe (not illustrated) can be formed in a straight or curved shape. In this case, the n−1 spray nozzles 510 can be arranged in a line at predetermined intervals at the second nozzle pipe (not illustrated) having the straight or curved shape.

As another example, the second nozzle pipe (not illustrated) can be implemented into a polygonal shape such as a triangle, a circular shape, a radial shape, or the like. In this case, the arrangement of the n−1 spray nozzles 510 can be changed in various forms depending on the shape of the second nozzle pipe (not illustrated) having the polygonal shape, the circular shape, the radial shape, or the like.

In the second spray nozzle unit 500, a pressure of the solvent stream sprayed through the n−1 spray nozzles 510 can be 0.01 MPa to 1 MPa, 0.1 MPa to 0.5 MPa, or 0.1 MPa to 0.3 MPa. When the solvent stream is sprayed at the pressure within the above ranges, the entrainment of the non-vapor in the reactor 100 can be effectively removed.

According to an exemplary embodiment of the present invention, a spray angle of the bottom discharge stream of the gas-liquid separator 200 sprayed from the spray nozzles 410 formed in the first spray nozzle unit 400 can be different from a spray angle of the solvent stream sprayed from the spray nozzles 510 formed in the second spray nozzle unit 500. As such, a spray angle of the spray nozzle 410 formed in the first spray nozzle unit 400 and a spray angle of the spray nozzle 510 formed in the second spray nozzle unit 500 are set to be different from each other, such that the entrainment of the non-vapor in the reactor 100 can be more effectively removed. Specifically, the first spray nozzle unit 400 and the second spray nozzle unit 500 are formed in multiple stages, and the spray angles of the spray nozzles 410 and 510 are controlled to be different from each other, such that the number of required spray nozzles can be reduced and the entrainment of the non-vapor in the reactor 100 can be effectively removed.

The liquid stream is sprayed from each of the spray nozzles 410 and 510 formed in the first spray nozzle unit 400 and the second spray nozzle unit 500, respectively, at a predetermined angle. In this case, an angle at which the liquid is sprayed from an outlet of the nozzle can be defined as the spray angle. When the spray angle is large, the liquid can be sprayed in a wider area. When the spray angle is small, the liquid can be sprayed in a narrow area, and the liquid can thus be intensively sprayed to a specific range. Such a spray angle can be determined depending on an inner pressure or an inner structure of the nozzle, and the nozzle can be set so that the liquid is sprayed at a desired spray angle.

The spray angle of the bottom discharge stream of the gas-liquid separator 200 sprayed from the spray nozzles 410 formed in the first spray nozzle unit 400 can be 30° to 90°, 50° to 90°, or 70° to 90°. As such, the spray angle of the bottom discharge stream of the gas-liquid separator 200 sprayed from the spray nozzles 410 formed in the first spray nozzle unit 400 is adjusted to a relatively small angle as the above ranges, such that the entrainment of the polymer non-vapor which is a solid substance having a relatively heavy weight in the mixed vapor (vapor+non-vapor) rising in a non-uniform state by vortex generated in a region adjacent to the inner wall of the reactor 100 can be intensively removed.

In addition, the spray angle of the solvent stream sprayed from the spray nozzles 510 formed in the second spray nozzle unit 500 can be 91° to 120°, 100° to 120°, or 110° to 120°. As such, the spray angle of the solvent stream sprayed from the spray nozzles 510 formed in the second spray nozzle unit 500 is adjusted to a relatively large angle as the above ranges, such that the solvent can be sprayed with respect to the mixed vapor which rises to the central region of the reactor 100 and is not removed through the first spray nozzle unit 400 in a wider area. Thus, the residual non-vapor such as liquid droplets having a relatively light weight can be effectively removed.

According to an exemplary embodiment of the present invention, the apparatus for preparing oligomer can further include devices required for the oligomer production such as a valve (not illustrated), a condenser (not illustrated), a reboiler (not illustrated), a pump (not illustrated), a cooling facility (not illustrated), a filter (not illustrated), a stirrer (not illustrated), a separation device (not illustrated), a compressor (not illustrated), and a mixer (not illustrated), if necessary.

Hereinabove, the apparatus for preparing oligomer according to the present invention has been described and illustrated in the drawing. However, the description and the illustration of the drawing are for only essential components for understating the present invention, and processes and apparatuses not separately described and illustrated can be properly applicable and used for implementing the apparatus for preparing oligomer, in addition to the processes and apparatuses described and illustrated in the drawing.

The invention claimed is:
1. An apparatus for preparing oligomer, comprising:
   a reactor receiving a monomer stream and a solvent stream, allowing an oligomerization reaction to proceed, and discharging a gaseous first discharge stream and a liquid second discharge stream;

a gas-liquid separator separating the gaseous first discharge stream of the reactor into a liquid phase and a gas phase and feeding a liquid bottom discharge stream to the reactor;

a first transfer line extending from a bottom of the gas-liquid separator to a region spaced apart from an inner wall of the reactor at a position higher than a reaction region inside the reactor and transferring the liquid bottom discharge stream of the gas-liquid separator;

a solvent transfer line transferring the solvent stream to the reactor;

a second transfer line separated from the solvent transfer line and transferring a part of the solvent stream to a region spaced apart from the inner wall of the reactor at a position higher than a height at which the first transfer line inside the reactor is formed;

a first spray nozzle unit connected to an end of the first transfer line inside the reactor and having n spray nozzles formed to be spaced apart from each other, wherein n is an integer of 2 or more; and a second spray nozzle unit connected to an end of the second transfer line inside the reactor and having n−1 spray nozzles formed to be spaced apart from each other, wherein a spray angle of the liquid bottom discharge stream of the gas-liquid separator sprayed from the spray nozzles formed in the first spray nozzle unit is 30° to 90°, and wherein a spray angle of the solvent stream sprayed from the spray nozzles formed in the second spray nozzle unit is 91° to 120°.

2. The apparatus for preparing oligomer of claim 1, wherein the gaseous first discharge stream of the reactor is fed to the gas-liquid separator after passing through a condenser.

3. The apparatus for preparing oligomer of claim 1, wherein:
  each of the n spray nozzles formed in the first spray nozzle unit is formed to be spaced apart from each other at predetermined intervals, and
  the n−1 spray nozzles formed in the second spray nozzle unit are formed in a region between lines vertical to positions at which the n spray nozzles of the first spray nozzle unit are formed.

4. The apparatus for preparing oligomer of claim 1, wherein n is an integer of 2 to 20.

5. The apparatus for preparing oligomer of claim 1, wherein a spray angle of the liquid bottom discharge stream of the gas-liquid separator sprayed from the spray nozzles formed in the first spray nozzle unit is different from a spray angle of the solvent stream sprayed from the spray nozzles formed in the second spray nozzle unit.

6. The apparatus for preparing oligomer of claim 1, wherein:
  the first spray nozzle unit includes a first nozzle pipe connecting the n spray nozzles formed in the first spray nozzle unit and the first transfer line to each other, and
  the second spray nozzle unit includes a second nozzle pipe connecting the n−1 spray nozzles formed in the second spray nozzle unit and the second transfer line to each other.

* * * * *